US00PP18706P2

(12) United States Plant Patent
Bradford

(10) Patent No.: US PP18,706 P2
(45) Date of Patent: Apr. 1, 2008

(54) NECTARINE TREE NAMED 'PEARLICIOUS III'

(50) Latin Name: *Prunus persica*
Varietal Denomination: Pearlicious III

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/637,893

(22) Filed: Dec. 13, 2006

(51) Int. Cl.
*A01H 5/00* (2006.01)

(52) U.S. Cl. ..... Plt./189

(58) Field of Classification Search ..... Plt./189
See application file for complete search history.

(56) References Cited

U.S. PATENT DOCUMENTS

PP7,421 P 1/1991 Bradford
PP14,242 P2 10/2003 Bradford

*Primary Examiner*—Kent Bell

(57) ABSTRACT

The present invention relates to a new and distinct variety of nectarine tree, *Prunus persica,* broadly characterized by a large size, vigorous, hardy, self-fertile, productive and regular bearing tree. The fruit matures under the ecological conditions described in mid June, with first picking on Jun. 14, 2006. The fruit is uniformly large in size, sub-acidic and very sweet in flavor, globose in shape, freestone in type, very firm in texture, white in flesh color, and mostly red in skin color.

1 Drawing Sheet

Botanical classification: *Prunus persica.*
Variety denomination: 'PEARLICIOUS III'.

BACKGROUND OF THE VARIETY

In a continuing effort to improve the quality of shipping fruits, I, the inventor, typically hybridize a large number peach, nectarine, plum, apricot, and cherry seedlings each year. The present invention relates to a new and distinct variety of nectarine tree, which has been denominated varietally as 'PEARLICIOUS III'.

The present variety was hybridized by me in 2001 as a first generation cross using 'Rose Diamond' (U.S. Plant Pat. No. 7,421) nectarine as the selected seed parent and an unnamed white freestone nectarine as the selected pollen parent. I used embryo rescue techniques to germinate the seeds from the fruit of this cross, grew them as seedlings on their own root in my greenhouse, and upon reaching dormancy transplanted them to a cultivated area of my experimental orchard located near Le Grand, Calif., in Merced County (San Joaquin Valley). During the fruit evaluation season of 2003 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its selected seed parent, 'Rose Diamond' nectarine, by producing nectarines that are nearly globose in shape, firm in texture, and nearly full red in skin color, but is distinguished therefrom by producing fruit that is larger in size, white instead of yellow in flesh color, and that matures about ten days later.

The present variety is most similar to 'Diamond Pearl' (U.S. Plant Pat. No. 14,242) nectarine, by producing nectarines that are nearly globose in shape, very firm in texture, white in flesh color, and nearly full red in skin color, but is distinguished therefrom by having globose instead of reniform glands, by having a sweet instead of bitter tasting kernel, and by producing nectarines that are freestone instead of clingstone in type.

SUMMARY OF VARIETY

In summary, the present variety is characterized by a large size, vigorous, hardy, self-fertile, productive and regular bearing tree. The fruit matures under the ecological conditions described in mid June, with first picking on Jun. 14, 2006. The fruit is uniformly large in size, sub-acidic and very sweet in flavor, globose in shape, freestone in type, very firm in texture, white in flesh color, and mostly red in skin color.

DRAWING

The accompanying photograph consists of four whole fruits positioned to display the characteristics of the skin color and form, one fruit divided around the suture plane to reveal the flesh and stone, two insets to reveal buds and a blossom, and various leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif. and was developed at the state of firm ripe on Jun. 18, 2006, on the original tree during its fifth growing season. All major color code designations are by reference to the Inter-Society Color Council, National Bureau of Standards. Common color names are also used occasionally.

Tree

Size: Large, reaching and maintaining a height of 11' [3.35 m.] and a spread of 10' [3.05 m.] after five growing season utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Pruned to a central leader form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 600 hours.

Trunk:

*Size.*—Medium, reaching a maximum diameter of 4" [102 mm.] after the fifth growing season.

*Texture.*—Shaggy.

*Bark color.*—A Grayish brown [61. gy.Br] was Deep brown [56. deep Br] variegation.

*Lenticels.*—Approximate Number Per Square Inch: 6. Color: Dark orange yellow [72. d.OY]. Typical Size: 3/16" [4.8 mm.] to 1/2" [12.7 mm.]. Shape: Eye-shaped to elongated.

Branches:

*Size.*—Diameter of first lateral is 1 3/8" [35 mm.] measured 12" from the central leader.

*Texture.*—Smooth on first and second year wood, increasing roughness with age.

*Color.*—1st Year Wood Topside: Grayish red [19. gy.R]. 1st Year Wood Underside: Brilliant yellow green [116. brill.YG]. Older Wood: Deep yellowish brown [75. deep yBr].

*Lenticels.*—Number Per Square Inch: More than 60 on second year wood. Color: Light yellowish brown [76. l.yBr]. Typical size: 1/64" [0.4 mm.] to 3/32" [2.4 mm.] on second year wood. Shape: Elongated.

Leaves:

*Size.*—Large. Average Length: 6 1/2" [165 mm.]. Average Width: 1 3/4" [44 mm.].

*Arrangement.*—Alternate.

*Thickness.*—Medium.

*Form.*—Elliptical.

*Apex.*—Acuminate.

*Base.*—Acute, with a base angle of 80 to 85 degrees.

*Surface.*—Smooth.

*Color.*—Dorsal Surface: Deep yellow green [118. deep YG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: 1/2" [12.7 mm.]. Average Thickness: 1/16" [1.6 mm.]. Color: Strong yellow green [117. s.YG].

*Stipules.*—Number: Usually 2 per leaf, up to 6 per growing tip. Average Length: 1/4" [6.4 mm.]. Color: Brilliant yellow green [116. brill.YG] becoming Moderate reddish brown [43. m.rBr] with maturity.

*Glands.*—Number: 2 to 5 per leaf. Position: Alternately positioned on petiole and base of blade. Size: Medium. Form: Globose. Color: Very yellow green [115. v.YG] becoming Dark reddish brown [44. d.rBr] with age.

*Leaf buds.*—Pointed, medium in size.

Flower buds:

*Hardiness.*—Hardy, with respect to central California winters.

*Diameter.*—Typically 3/8" [9.5 mm.] 1 week before bloom.

*Length.*—Typically 11/16" [17.5 mm.] 1 week before bloom.

*Form.*—Not appressed.

*Surface.*—Pubescent.

*Color.*—Light purplish pink [249. l.pPk].

Flowers: Perfect, complete, perigynous, usually a single pistil, typically thirty or more stamens, five sepal and petal locations alternately positioned.

*Type.*—Showy, large.

*Average flower diameter.*—1 7/8" [47.6 mm.].

*Number of petals.*—Usually five, extra petal fragments and a few double blossoms observed occasionally.

*Petal shape.*—Circular to oval.

*Petal margin.*—Somewhat wavy.

*Average petal diameter.*—13/16" [20.6 mm.].

*Average petal length.*—13/16" [20.6 mm.].

*Petal apex.*—Rounded.

*Petal base.*—Rounded to somewhat truncate.

*Petal color.*—Pale pink [7. p.Pk] toward the apex, Light pink [4. l.Pk] toward the base.

*Anther color.*—Dark reddish orange [38. d.rO] over a Light yellow [86.6 l.Y] center at bloom onset.

*Stigma color.*—Light greenish yellow [101. l.gY].

*Sepal color.*—Dark purplish red [259. d.pR].

*Sepal length.*—1/4" [6.4 mm.].

*Sepal width.*—3/16" [4.8 mm.].

*Average pistil length.*—13/16" [20.6 mm.].

*Average stamen length.*—5/8" [15.9 mm.].

*Fragrance.*—Moderate.

*Blooming period.*—medium, five days after 'Rose Diamond' (U.S. Plant Pat. No. 7,421) nectarine.

*Onset of bloom.*—One percent on Feb. 27, 2006.

*Date of full bloom.*—Mar. 9, 2006.

*Duration of bloom.*—One to two weeks, dependent on ambient temperature.

*Number per cluster.*—1 to 3 with single flowers most common.

FRUIT

Maturity when described: Firm ripe, Jun. 18, 2006.

Date of first picking: Jun. 14, 2006.

Date of last picking: Jun. 24, 2006.

Size: Uniform, large.

*Average diameter axially.*—3" [76 mm.].

*Average diameter across suture plane.*—2 7/8" [73 mm.].

*Average diameter across cheek plane.*—2 15/16" [75 mm.].

*Typical weight.*—7.8 ounces [221 grams].

Form: Globose.

*Longitudinal section form.*—Elliptical to slightly obovate.

*Axial view.*—Round.

Suture: A shallow groove extending from the base to beyond the apex, sharper in the stem cavity and toward the apex.
Ventral surface: Rounded slightly, lipped toward the apex.
Lips: Fairly equal.
Cavity: Flaring, circular, suture showing on one side, Pale Yellow [89. p.Y] stem markings typical.
*Depth.*—¼" [6.4 mm.].
*Breadth.*—⅞" [22.2 mm.].
Base: Truncate.
Apex: Rounded.
Pistil point: Apical, short, usually depressed within the suture.
Stem: Medium.
*Average length.*—⅜" [9.5 mm.].
*Average width.*—3⁄16" [4.8 mm.].
Skin:
*Thickness.*—Medium.
*Surface.*—Smooth.
*Tenacity.*—Tenacious to flesh.
*Astringency.*—Non-astringent.
*Tendency to crack.*—None observed.
*Color.*—Dark red [16. d.r] smoothly blending into a Moderate red [15. m.R] background with heavy Yellowish white [92. y.White] freckling toward the apex.
Flesh:
*Color.*—White [263. White] from the skin to the stone with the very slightest amount of Moderate red [15. m.R] streaking very near the apex of the stone.
*Surface of pit cavity.*—Covered with Yellowish white [92. y.White] fibers.
*Amygdalin.*—Moderate.
*Juice.*—Moderate, rich.
*Texture.*—Firm, crisp.
*Fibers.*—Abundant, fine.
*Ripens.*—Earlier at the apex.
*Flavor.*—Sub-acidic and sweet, typically 18 to 20 brix, balanced with some traditional nectarine flavor.
*Aroma.*—Moderate.
*Eating quality.*—Excellent.

STONE

Type: Freestone.
Form: Oval.
Hilum: Narrow.
Base: Straight.
Apex: Obtuse to rounded.
Sides: Equal.
Surface: Irregularly furrowed toward the apex, pitted from base to above center.
Ridges: Rounded.
External color: Strong yellowish brown [74. s.yBr].
Pit wall color when cracked: Light yellowish brown [76. l.yBr].
Cavity surface color: Dark orange yellow [72. d.OY].
Average pit wall thickness: ¼" [6.4 mm.].
Average width: 1 1⁄16" [27.0 mm.].
Average length: 1 7⁄16" [36.5 mm.].
Average breadth: ⅝" [15.9 mm.].
Tendency to split: None observed.
Kernel:
*Form.*—Oval.
*Skin color.*—Strong yellowish brown [74. s.yBr.].
*Pellicle color.*—Deep yellowish brown [75. Deep y.Br].
*Vein color.*—Deep yellowish brown [75. Deep y.Br].
*Taste.*—Sweet.
*Viable.*—Yes.
*Average width.*—7⁄16" [11.1 mm.].
*Average length.*—11⁄16" [17.5 mm.].
*Amygdalin.*—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Diamond Pearl' (U.S. Plant Pat. No. 14,242) nectarine, by producing nectarines that are nearly globose in shape, very firm in texture, white in flesh color, and nearly full red in skin color, but is distinguished therefrom by having globose instead of reniform glands, by having a sweet instead of bitter tasting kernel, and by producing nectarines that are freestone instead of clingstone in type.

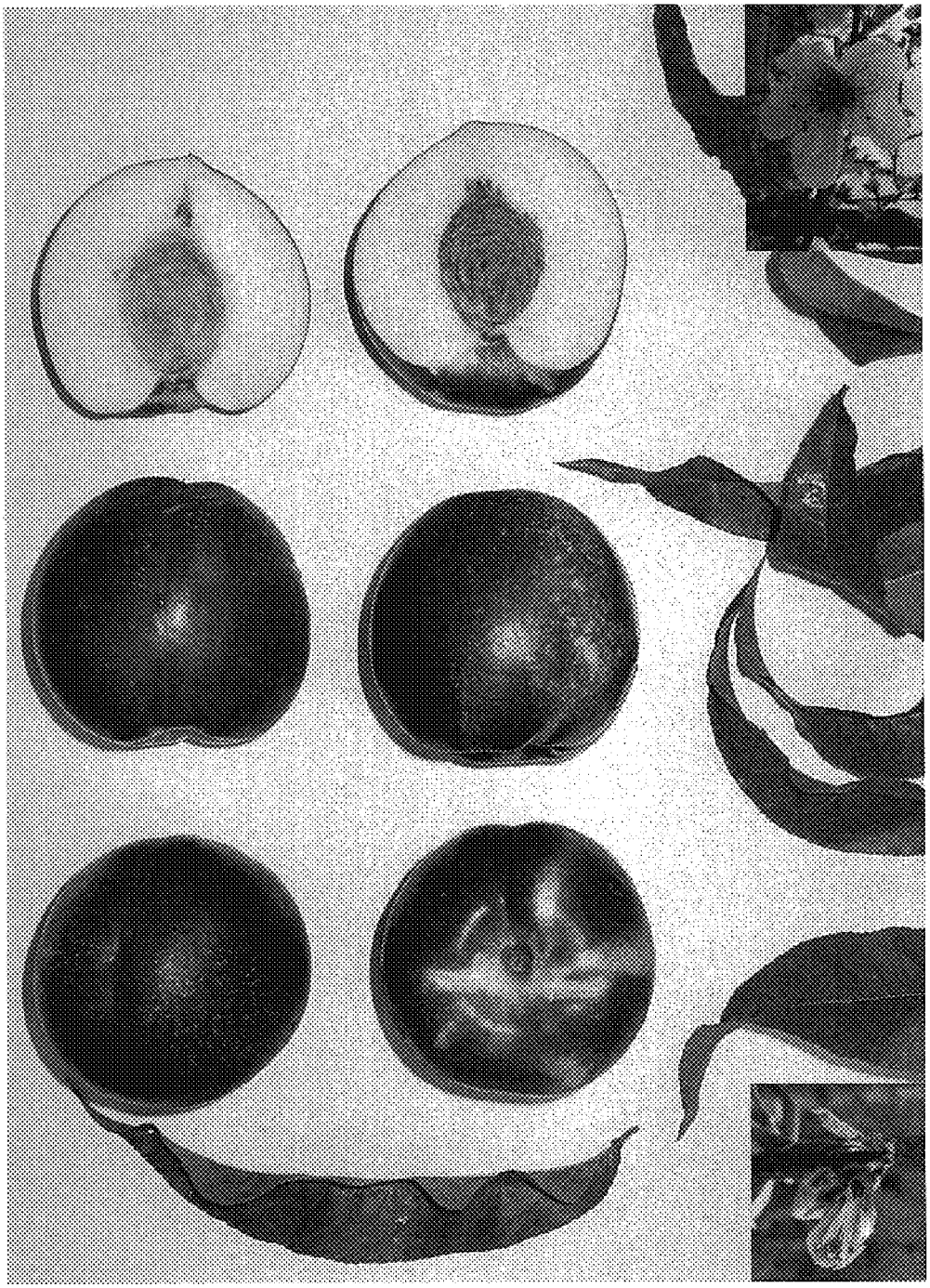

* * * * *